US009212200B2

(12) United States Patent
Mandelbaum et al.

(10) Patent No.: US 9,212,200 B2
(45) Date of Patent: Dec. 15, 2015

(54) NANOSTRUCTURE HAVING METAL NANOPARTICLES AND METHOD OF ASSEMBLY THEREOF

(71) Applicant: BAE Systems Information and Electronic Systems Integration Inc., Nashua, NH (US)

(72) Inventors: Idan Mandelbaum, Columbia, MD (US); Tadd C. Kippeny, Mount Airy, MD (US)

(73) Assignee: BAE Systems Information and Electronic Systems Integration Inc., Nashua, NH (US)

( * ) Notice: Subject to any disclaimer, the term of this patent is extended or adjusted under 35 U.S.C. 154(b) by 179 days.

(21) Appl. No.: 13/986,178

(22) Filed: Apr. 8, 2013

(65) Prior Publication Data

US 2014/0135516 A1    May 15, 2014

Related U.S. Application Data

(63) Continuation-in-part of application No. 12/379,495, filed on Feb. 24, 2009, now abandoned.

(51) Int. Cl.
*C07F 19/00* (2006.01)
*B82Y 20/00* (2011.01)

(52) U.S. Cl.
CPC *C07F 19/00* (2013.01); *B82Y 20/00* (2013.01)

(58) Field of Classification Search
CPC .............................. C07F 19/00; B82Y 20/00
USPC ............................ 556/27, 28, 51, 57, 110, 58
See application file for complete search history.

(56) References Cited

PUBLICATIONS

B.V. Enustun et al., "Coagulation of Colloidal Gold," J. Am. Chem. Soc., vol. 85, p. 3317-3328, 1963.
T. Kippeny, "Exciton Dynamics in Cadmium Selenide/Zinc Selenide Core/Core-Shell Nanocrystals as Effected by Surface Ligands Modification Using Femtosecond Fluorescence Upconversion," Dissertation, Vanderbilt University, 2005.
S.K. Park, et al., "Preparation of silica nanopartides: determination of the optimal synthesis conditions for small and uniform particles," Colloids and Surfaces A: Physicochemical and Engineering Aspects, vol. 197, Issues 1-3, 4, Feb. 2002, pp. 7-17.
L.M. Liz-Marzan, et al. in "Synthesis of Nanosized Gold-Silica Core-Shell Particles" (Langmuir, vol. 12, 4329-4335, 1996.
Bai et al., "A Spectrum-Narrowed, Wavelength and Temperature Stabilized Broad Area Laser Using a Subwavelength Resonant Grating Filter Feedback" The 19th Annual Meeting of the IEEE LEOS (LEOS'06), Montreal Canada, (2006), pp. 659-660.
Bjork et al., "Definition of a Laser Threshold" Physical Review A, (1994), vol. 50, No. 2, pp. 1675-1680.
Chu, "Physical Limitations of Omni-Directional Antennas" Journal of Applied Physics, (1948), vol. 19, pp. 1163-1175.

(Continued)

*Primary Examiner* — Porfirio Nazario Gonzalez
(74) *Attorney, Agent, or Firm* — Daniel J. Long

(57) ABSTRACT

A nanostructure and method for assembly thereof are disclosed. An exemplary nanostructure includes a photocatalytic nanoparticle; a first tier of metal nanoparticles, each metal nanoparticle of the first tier being linked about the photocatalytic nanoparticle; and a second tier of metal nanoparticles, each metal nanoparticle of the second tier being linked to one of the metal nanoparticles of the first tier and located a distance from the photocatalytic nanoparticle greater than a distance between a metal nanoparticle of the first tier and the photocatalytic nanoparticle.

21 Claims, 5 Drawing Sheets

(56) References Cited

PUBLICATIONS

Citrin, "Coherent Excitation Transport in Metal-Nanopartide Chains" Nano Letters, (2004), vol. 4, No. 9, pp. 1562-1565.

Citrin, "Subwavelength Nanoplasmonic Ring Resonators" J. Opt. Soc. Am. B, (2005), vol. 22, No. 8, pp. 1763-1769.

Citrin, "Plasmon-Polariton Transport in Metal-Nanopartide Chains Embedded in a Gain Medium" Optics Letters, (2006), vol. 31, No. 1, pp. 98-100.

Govorov et al., "Exciton-Plasmon Interaction and Hybrid Exctions in Semiconductor-Metal Nanopartide Assemblies" Nano Letters, (2006), vol. 6, No. 5, pp. 984-994.

Gradecak et al., "GaN Nanowire Lasers with Low Lasing Thresholds" Applied Physics Letters, (2005), vol. 87, pp. 173111-1 to 173111-3.

Hsung et al., "Thiophenol Protecting Groups for the Palladium-Catalyzed Heck Reaction: Efficient Syntheses of Conjugated Arylthiols" Tetrahedron Letters, (1995), vol. 36, No. 26, pp. 4525-4528.

Hsung et al., "Synthesis and Characterization of Unsymmetric Ferrocene-Terminated Phenylethynyl Oligomers Cp2FE-[C=C-C6H4]n-X (X=SH, SMe, and SO2Me)" Organometallics, (1995), vol. 14, pp. 4808-4815.

Kneipp et al., "Surface-Enhanced Raman Scattering and Biophysics" Journal of Physics: Condensed Matter, (2002), vol. 14, pp. R597-R624.

Lavastre et al., "Selective and Efficient Access to Ortho, Meta and Para Ring-Substituted Phenylacetylene Derivatives R-[C=C-C6H4]x-Y (Y: H, No2, CN, I, NH2)" Tetrahedron, (1997), vol. 53, No. 22, pp. 7595-7604.

Lee et al., "Bioconjugated Ag Nanopartides and CdTe Nanowires: Metamaterials with Field-Enhanced Light Absorption" Angewandte Chemie Int. Ed., (2006), vol. 45, pp. 4819-4823.

Lu et al., "Self-Similar Chain of Metal Nanospheres as Efficient Nanolens" Phys. Rev. Lett., (2003), vol. 91, No. 22, pp. 227402.

Lu et al., "Lasing of CdSexS1-x Quantum Dots in a Glass Spherical Microcavity" Journal of Physics: Condensed Matter, (2002), vol. 14, pp. 6395-6401.

Murray et al., "Synthesis and Characterization of Monodisperse Nanocrystal and Close-Packed Nanocrystal Assemblies" Annu. Rev. Mater. Sci., (2000), vol. 30, pp. 545-610.

Peng et al., "Epitaxial Growth of Highly Luminescent CdSe/CdS Core/Shell Nanocrystals with Photostability and Electronic Accessibility" J. Am. Chem. Soc. (1997), vol. 119, pp. 7019-7029.

Slocik et al., "Optical Characterization of Bio-Assembled Hybrid Nanostructures" Supramolecular Chemistry, (2006), vol. 18, No. 5, pp. 415-421.

Stober et al., "Controlled Growth of Monodisperse Silica Spheres in the micron Size Range" Journal of Colloid and Interface Science, (1968), vol. 26, pp. 62-69.

Stuczynski et al., "Formation of Metal-Chalcogen Bonds by the Reaction of Metal Alkyls with Silyl Chalcogenides" Inorganic Chemistry, (1989), vol. 28, No. 25, pp. 4431-4432.

Zhang et al., "Fabrication of InAs Quantum dots in AlAs/GaAs DBR Pillar Microcavities for Single Photon Sources" Journal of Applied Physics, (2005), vol. 97, pp. 073507-1 to 073507-7.

Zhu et al., "Facile One-Pot Synthesis of Gold Nanoparticles Stabilized with Bifunctional Amino/Siloxy Ligands" Journal of Colloid and Interface Science, (2005), vol. 287, pp. 360-365.

NANOSTRUCTURE HAVING METAL NANOPARTICLES AND METHOD OF ASSEMBLY THEREOF

RELATED APPLICATIONS

This application is a continuation-in-part and claims the benefit of U.S. application Ser. No. 12/379,495, filed Feb. 24, 2009 which is herein incorporated by reference in its entirety for all purposes.

FIELD OF THE INVENTION

A nanostructure including metal nanoparticles, and a method of assembling a nanostructure including metal nanoparticles, are disclosed.

BACKGROUND

Gold metal nanoparticles have been used as a pigment to, for example, stain glass. More recently, there has been research into developing metal nanostructure assemblies, including structures made from noble metals such as gold and silver. For example, it is known to use an electromagnetic wave to excite a strong resonance condition in metal nanoparticles, which can lead to enhanced, localized electromagnetic fields.

SUMMARY

A nanostructure is disclosed which includes a photocatalytic nanoparticle, a first tier of metal nanoparticles, and a second tier of metal nanoparticles. Each metal nanoparticle of the first tier is linked about the photocatalytic nanoparticle, and each metal nanoparticle of the second tier is linked to one of the metal nanoparticles of the first tier and is located a distance from the photocatalytic nanoparticle that is greater than a distance between a metal nanoparticle of the first tier and the photocatalytic nanoparticle.

An exemplary method is also disclosed for assembling an exemplary nanostructure. The method includes attaching a first linker about a photocatalytic nanoparticle, attaching a second linker to a first metal nanoparticle, and attaching the first metal nanoparticle about the photocatalytic nanoparticle by connecting the first linker and the second linker. A second metal nanoparticle is attached to the first metal nanoparticle by attaching a third linker to the first metal nanoparticle, attaching a fourth linker to the second metal nanoparticle and connecting the third linker and the fourth linker.

BRIEF DESCRIPTION OF THE DRAWINGS

The accompanying drawings, which are included to provide a further understanding and are incorporated in and constitute a part of this specification, illustrate embodiments of the invention that together with the description serve to explain the principles of the invention. In the drawings.

DETAILED DESCRIPTION

Figure 1:
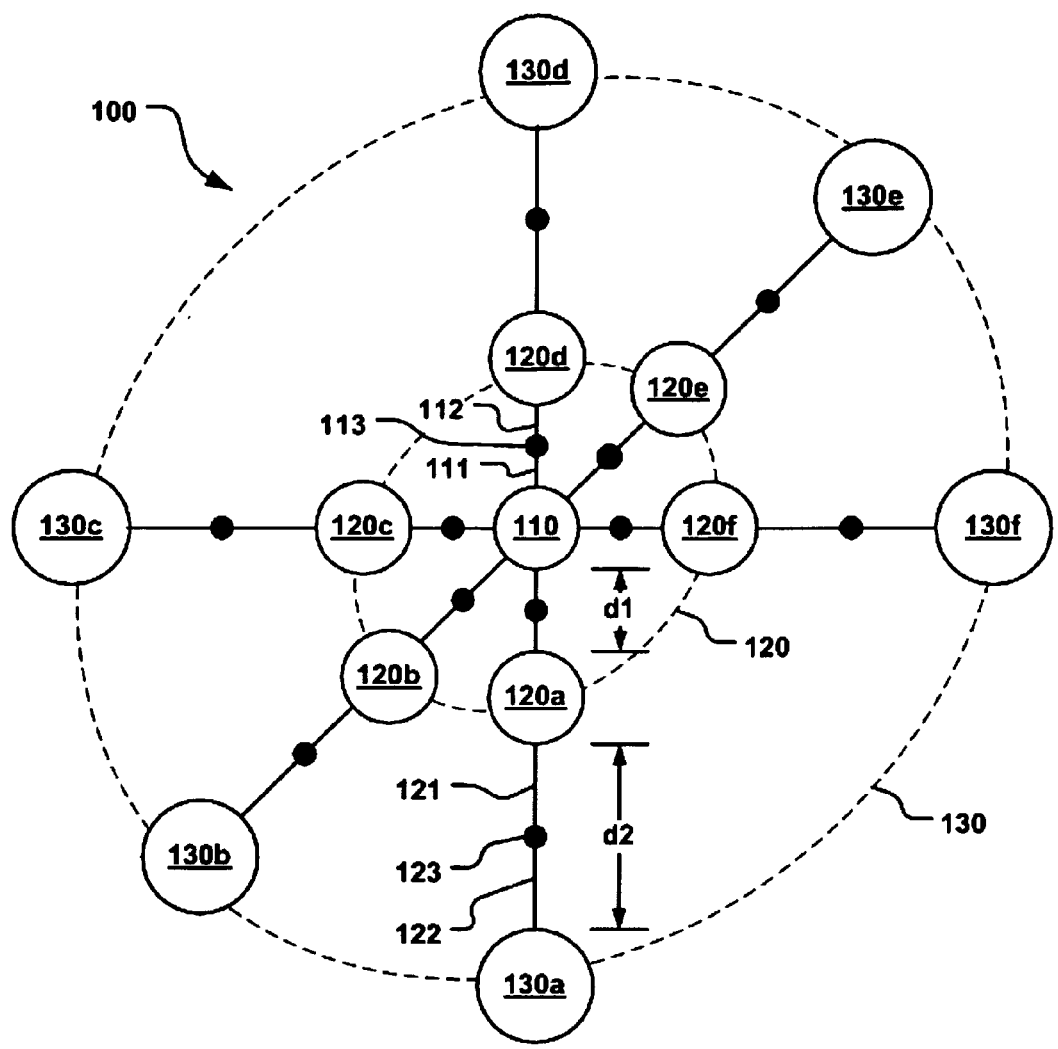
FIG. 1 is a diagram of an exemplary nanostructure having two tiers of metal nanoparticles.

FIG. 1 is a diagram of an exemplary nanostructure 100, including a photocatalytic nanoparticle 110, first tier 120 of metal nanoparticle, and a second tier 130 of metal nanoparticles. Each metal nanoparticle 120a to 120f of the first tier is linked about the photocatalytic nanoparticle 110 (e.g., attached to the photocatalytic nanoparticle or about a void created to represent the photocatalytic nanoparticle), and each metal nanoparticle 130a to 130f of the second tier is linked to one of the metal nanoparticles 120a to 120f of the first tier, respectively. The metal nanoparticles of the second tier 130 are located a further distance from the photocatalytic nanoparticle 110 than a distance between the metal nanoparticles of the first tier 120 and the photocatalytic nanoparticle 110.

Embodiments of a nanostructure including first and second metal nanoparticle tiers can confine light approaching the nanostructure in almost any direction and excite surface plasmons. These surface plasmons, in turn, can produce a focused electric field in a resonance cavity comprising the first tier 120 and second tier 130.

The two tiers of metal nanoparticles 120, 130 shown in FIG. 1 can act as a three-dimensional feedback structure or resonance cavity that amplifies the electric field within the resonance cavity via electromagnetic enhancement. The enhanced field can be highly localized at a place serving as a "hot spot" for the field enhancement and a site for locating the photocatalytic nanoparticle 110. These metal nanoparticle assemblies can be, for example, any kind of metal nanoparticle structure assembly that has a dielectric constant having a negative real part. Examples of metals for the metal nanoparticles include gold, silver, aluminum, copper, titanium, chromium, and other metals capable of supporting surface plasmons.

The photocatalytic nanoparticle 110 is a material having the capability of producing excitons, such as a semiconductor material, or any other desired particle to be exposed to an enhanced field. For example, photocatalytic nanoparticle 110 may be a light-emitting semiconductor material, such as II-VI or III-V semiconductor material, for example CdSe, GaAs, InSb, or $LiNbO_3$, or other types of semiconductor materials. In other embodiments, the nanoparticle to which the first tier 120 of metal nanoparticles 120a to 120f is attached can be a magnetic particle, or a place-holder nanoparticle that does not need to interact with the surrounding feedback structure and which can be removed if desired. This placeholder nanoparticle can be on the order of 1 nm or smaller, for example although the placeholder nanoparticle also may be larger than 1 nm.

The photocatalytic nanoparticle 110 can also be a core semiconductor nanoparticle covered with a shell layer of another wider bandgap semiconductor material to form a core-shell heterostructure. For example, a CdSe semiconductor nanoparticle can serve as the core and a ZnS epitaxial layer can function as the shell in an exemplary heterostructure embodiment, although other semiconductor materials may be used to form the heterostructure. A heterostructure can minimize the number of surface traps, yield greater charge recombination (quantum yield), reduce leakage current, and improve injection characteristics.

By varying the number of tiers of metal nanoparticles, the relative sizes of the metal nanoparticles, and/or the distances between the metal nanoparticles, parameter values can be determined that allow for extraction of a maximum enhancement from a given nanoparticle configuration. For example, an exemplary nanostructure embodiment may include a metal nanoparticle and/or photocatalytic nanoparticle shape chosen to tune the structure to a particular resonant wavelength. Although the metal nanoparticles shown in FIG. 1 are depicted as spheres, the shape of a metal nanoparticle may be a rod, triangle, plate, pentagon, ellipsoid, or any other desired shape. Other parameters that may be controlled to increase electromagnetic field enhancement include varying the size of a metal nanoparticle and varying the size of metal nanoparticles from one tier group relative to another.

Keeping the distances between the nanoparticles proportional while increasing only the sizes of the nanoparticles can yield a high result gain increase that follows a power law with the sizes of the nanoparticles. The non-radiative decay rate does not necessarily increase correspondingly. By bringing the nanoparticles closer together for a given nanoparticle diameter set, the enhancement and non-radiative lifetime can, for example, increase exponentially.

The associated wavelength of a photocatalytic nanoparticle, for example, a semiconductor nanoparticle, may be adjusted by, for example, controlling a size (e.g., diameter) or shape of the nanoparticle to tune it to a desired emission or lasing wavelength. For example, a range of wavelengths from 490-620 nm, or lesser or greater, can be achieved for CdSe semiconductor nanocrystals by appropriately varying the diameter of the CdSe nanoparticle. Wider or narrower ranges of wavelengths can be achieved by using other semiconductor material compositions.

Referring to FIG. 1, the metal nanoparticles $120a$ to $120f$ and $130a$ to $130f$, and the photocatalytic nanoparticle 110 can be linked using organic linkers. A first linker 111, a second linker 112, and a connection point 113 between the first and second linkers, is provided between the photocatalytic nanoparticle 110 and each metal nanoparticle of tier 120. Third linker 121 and fourth linker 122 with an intermediate connection point 123 are provided between each metal nanoparticle of the first tier 120 and each metal nanoparticle of the second tier 130. The linkers connecting the photocatalytic nanoparticle 110 and the tiers of metal nanoparticles 120, 130 can be any organic ligand type, such as alkane linkers or polyethylene glycol (PEG) linkers, or another type of linker composed of organic material using attachment chemistry such as biotin-streptavidin, or amine and N-hydroxysuccinimide, etc.

While FIG. 1 shows nanostructure 100 as having metal nanoparticles $120a$ to $120f$ attached to six "sides" of a photocatalytic nanoparticle 110, with three orthogonal axes, other embodiments may be arranged on fewer or more axes and utilize a fewer or greater number of first and second tier nanoparticles per nanostructure to focus the field. The pattern of the overall nanostructures may be self-similar or any other type of pattern. Furthermore, some embodiments of nanostructure geometries may include more than two tiers to provide large localized field enhancements to amplify (e.g., increase or decrease (i.e., attenuate)) the electric field within the cavity. A distance d1 between a metal nanoparticle in tier 120 and the photocatalytic nanoparticle 110, and a distance d2 between a metal nanoparticle in tier 120 and a metal nanoparticle of tier 130 may be set to particular values to control field enhancement. Because the nanostructure 100 can be assembled smaller than the wavelength of light, for example, in sizes on the order of about 100-200 nm, it can have a very high packing density that permits its use in a variety of optical and/or other applications.

The nanostructure 100 can be assembled tier by tier starting from the semiconductor nanoparticles. The number of tiers can vary to control the enhancement, as well as the size and distances of the nanoparticles. The nanoparticles can be of any shape such as rods, sphere, triangles, etc. The pattern can be self-similar or any other type. Typical structure size is ~100-200 nm. The resonator structure could be embedded in polymer or other materials to provide support and increase the surrounding dielectric constant to provide additional enhancement.

Figure 2:
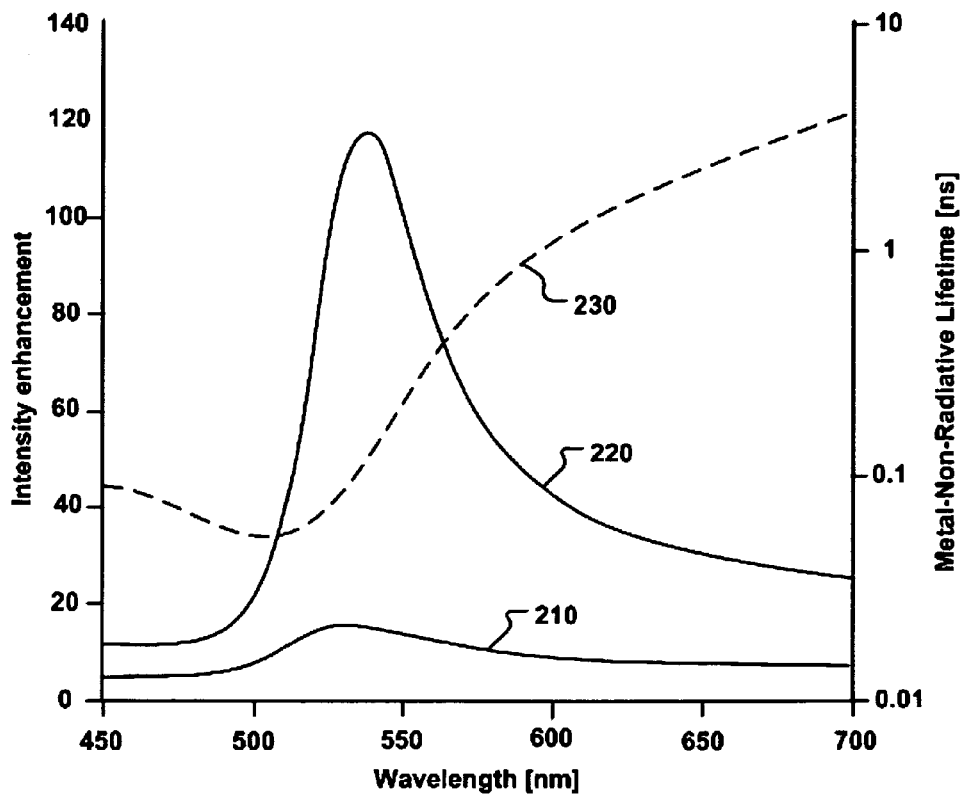
FIG. 2 shows graphs depicting exemplary intensity enhancement and metal non-radiative lifetimes in relation to wavelength for the differences in enhancement between single tier and multi-tier nanostructures.

FIG. 2 is a graph showing increased enhancement provided by a multi-tiered structure. As shown in FIG. 2, the graph 210 represents enhancement provided by a nanostructure having a first tier including two metal nanoparticles around a centrally located nanoparticle, and the graph 220 represents enhancement provided by adding a second tier of metal nanoparticles. The second tier provides two additional metal nanoparticles, resulting in a nanostructure with a total of four metal nanoparticles around a centrally located nanoparticle. As can be seen in FIG. 2, a nanostructure having only a single metal nanoparticle tier can provide a slight enhancement to the field. However, providing additional metal nanoparticle tiers can substantially increase enhancement. For example, providing a second metal nanoparticle tier located a distance further from the first metal nanoparticle tier can increase enhancement by up to an order of magnitude, or even greater.

Graph 230 of FIG. 2 represents a metal non-radiative lifetime (i.e., a rate at which the photocatalytic nanoparticle couples to non-radiative modes of the metal nanoparticles), resulting from both the one-tier structure corresponding to graph 210 and the two-tier structure corresponding to graph 220. A negligible increase in the metal non-radiative lifetime is incurred when a second tier is provided to the nanostructure, and the graph of the metal non-radiative lifetime for the one-tier structure coincides (overlaps) with the graph of the metal non-radiative lifetime for the two-tier structure, as shown in graph 230. As can be seen from FIG. 2, enhancement can be an order of magnitude greater when nanoparticles are provided further away from the photocatalytic nanoparticle with no substantial increase of coupling to the non-radiative lifetime. A significant increase in enhancement can be obtained almost independently of non-radiative loss, by optimizing the geometry of the system.

The plasmonic resonance condition can change with the dielectric constant of the environment surrounding the nanostructures. For instance, it is possible to tune the enhancement and/or the resonance wavelength of the nanostructure by changing the surrounding coating material and its corresponding dielectric. For example, an enhancement control variable may be the inclusion of a coating on the metal nanoparticles that has a different dielectric constant than the metal, for example, silicon dioxide. The nanostructures may be embedded in a polymer or other type of material to provide support to the nanostructure. This can permit another aspect of dielectric tuning. The frequency and/or intensity of the plasmonic resonance are known to be sensitive to the dielectric properties of the surrounding medium. For example, the plasmonic resonance can be sensitive to the refractive index of matter close to the nanostructure surface.

Figure 3:
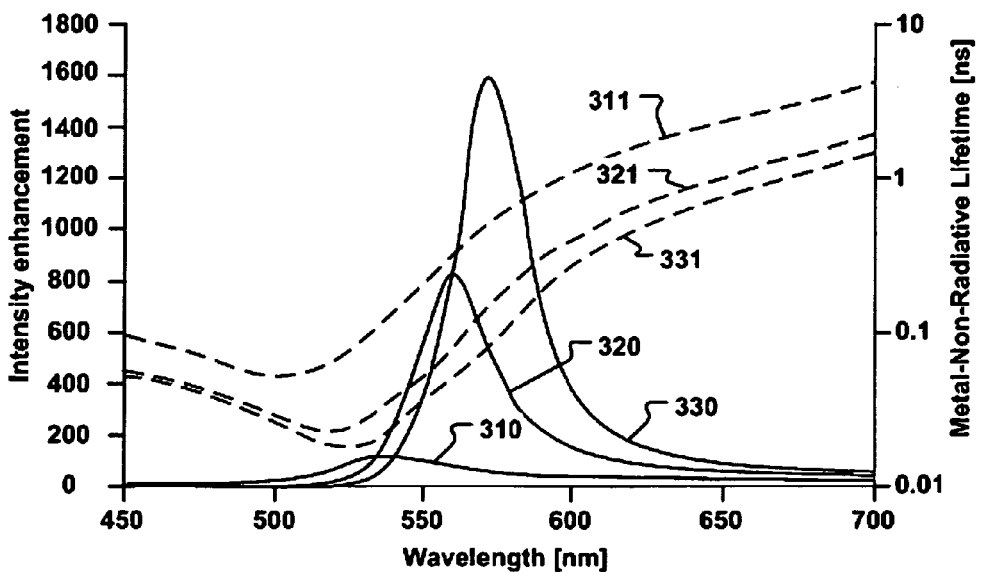
FIG. 3 shows graphs depicting exemplary effects of different types of dielectrics on a resonance wavelength of a nanostructure.

In FIG. 3, exemplary effects of a dielectric constant on the field enhancement of the nanostructure are shown, as well as the corresponding metal non-radiative lifetime. Graphs 310, 320, and 330 show intensity enhancements in the structure for the surrounding environments of air, glass, and water, respectively. As shown, when the dielectric constant of a material surrounding the nanostructure increases, the field enhancement correspondingly increases. The wavelength is also red-shifted as the dielectric constant of the surrounding material increases.

Additionally graphs 311, 321, and 331 of FIG. 3 represent the metal non-radiative lifetime corresponding to the non-radiative recombination rate for air, glass, and water, respectively. The non-radiative lifetime is shown as decreasing as the dielectric constant of the surrounding material increases. FIG. 3 shows that as the enhancement increases by an order of magnitude between air and glass, the non-radiative decay rate decreases only by a factor of 2. As enhancement grows, the photocatalytic nanoparticle non-radiative recombination rate into the metal grows as well, but much less than the actual enhancement, making dielectric shifting an efficient enhancement tuning method. Not only does the surrounding material provide a means for fine-tuning the enhancement strength and peak wave length, it can also provide support for the nanostructure.

Embodiments can include a nanoparticle having non-linear optical properties placed in a location of the focused high field (i.e., an enhanced field part of a nanostructure). Such nanoparticle materials may exhibit second or third order non-linearity. The optical properties of these non-linear nanoparticle materials can change as a function of a field in which the nanoparticle is placed. For example, use of non-linear materials for the nanoparticles in these structures would permit optic behavior that would normally occur at a high intensity to occur at lower (e.g., order of magnitude lower) intensity. This can substantially increase the potential applications for such a structure, such as more efficient optical switching A self-assembly method for creating this nanostructure can permit control to be retained over the number of layers, particle material composition, size, shape and/or overall development of the structure. This method can permit the structure to have a self-guided assembly that yields a high volume of product due to the selective nature of self-assembly chemistry (i.e. because each particle can selectively bind to another kind of particle, there can be a high yield of the desired product). This can be carried out by using organic linkers that can attach to another kind of linkers but not to themselves.

The first linkers that are attached about and/or to the photocatalytic nanoparticle are linkers that can favorably bond to a photocatalytic particle at one end and have a terminal functional group at the other end that favorably bonds to a second kind of linkers. The second kind of linkers can be selected to favorably bond to the metal nanoparticles at one end and include a functional group at the other end that will favorably bond to the first kind of linkers. These linkers can act analogously to magnets. Just as magnets have two distinct poles which only connect north to south, these linkers attach only at certain ends, and not others, and use these attachment points to connect together in a manner similar to stacking blocks.

In general, exemplary linkers will be of the form $H_2N$—R—COOH, where R is an organic linker of any desired length. The $H_2N$ (amine functional group) and the COOH (carboxylic acid functional group) are two exemplary terminal groups for the different types of linkers. This can permit the linkers to connect by peptide bonding (i.e., the bonding mechanism of amino acids), where the amine functional groups can, for example, bond to the carboxylic acid functional groups. In an exemplary embodiment, to form the first tier of metal nanoparticles around a photocatalytic nanoparticle, the photocatalytic particle can be coated with a plurality of first linkers having one of the two exemplary terminal groups. A plurality of first metal nanoparticles can be coated with a plurality of second linkers having the other of the two exemplary terminal groups. When these two types of nanoparticles are combined, the amine end of each of the linkers can combine with the carboxylic acid end of each of the linkers. This permits the nanoparticles to be linked in a way that can prevent the first tier metal nanoparticles from attaching to each other. To add an additional tier of metal nanoparticles, the first tier of metal nanoparticles is coated with a plurality of third linkers similar to or the same as the first linkers and a second tier of metal nanoparticles is coated with a plurality of fourth linkers similar to or the same as the second linkers. These linkers can be connected in the manner described above. In some embodiments, the nanostructure possesses two tiers; however, additional tiers of metal nanoparticles are possible and can be added in a manner similar to the first tier or in some other manner.

Figure 4A:
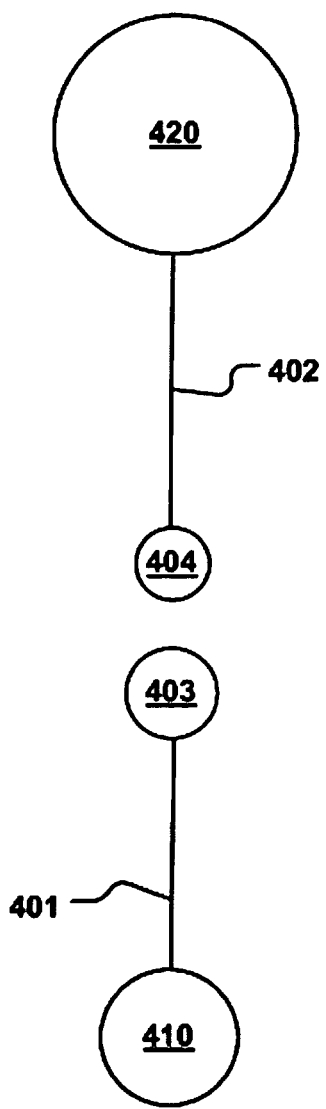
FIGS. 4A and 4B are high level diagrams showing an exemplary method of connecting a photocatalytic nanoparticle and a metal nanoparticle.
Figure 4B:
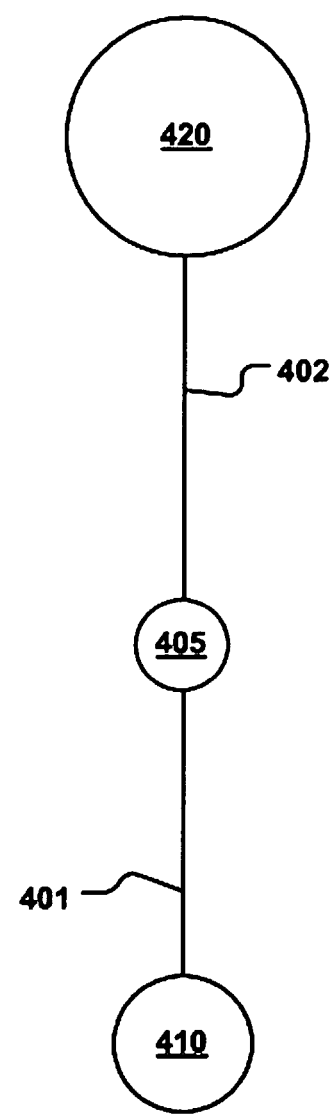

FIGS. 4A and 4B are diagrams showing an exemplary method for assembling (i.e., fabricating) a nanostructure. In FIG. 4A, photocatalytic nanoparticle 410 and metal nanoparticle 420 are shown. The photocatalytic nanoparticle has an organic linker 401 of any desired length attached to the nanoparticle, and the metal nanoparticle has a similar organic linker 402 of any desired length attached to the nanoparticle. Each of these linkers has a preferred terminal group attached to the other end.

For example, in FIG. 4A, a carboxylic acid functional group 403 is attached to the terminating end of the linker 401 connected to the photocatalytic nanoparticle and an amine functional group 404 is attached to the terminating end of the linker 402 connected to the metal nanoparticle.

In FIG. 4B, the amine and carboxylic acid functional groups of FIG. 4A have reformed to arrange the nitrogen of the amine group and the doubly bonded oxygen of the carboxylic acid group into group 405, effectively joining photocatalytic nanoparticle 410 and metal nanoparticle 420. In exemplary embodiments, the functional groups used for linking nanoparticles are amines and carboxylic acids. However, other suitable functional groups or chemical moieties can be used for connected different kinds of nanoparticles.

Because of the unique optical properties that can result from the interactions between the photocatalytic nanoparticle and the feedback structure, and the three-dimensional confinement these nanostructure assemblies are able to achieve, there is great potential for novel applications for these structures. Unlike a two-dimensional surface where a field can involve a certain polarization, where light entry can be limited to a certain direction, and where the amount of field inside can depend strongly on the direction (e.g., nanorods and nanowires that confine light only in two dimensions), the three-dimensional (3-D) aspect disclosed herein is substantially directionally independent. The 3-D structures described herein can confine light propagating from almost any direction, resulting in a capacity for a greatly enhanced localized electric field.

For example, the enhanced electric field created by a superstructure arranged around some light-emitting nanoparticle, such as a quantum dot or other photocatalytic nanoparticle, can be used to stimulate an increase in emission from that light-emitting nanoparticle. The 3-D super-structure can alternatively be arranged around a non-linear material, a magnetic material or even a molecule of heavy water, for the purpose of confining light and focusing the electromagnetic energy from all directions into localized spot. Additionally, while 3-D confinement is present in certain existing applications such as photonic band gap crystals, these crystals can include many defects, and their growth and resulting form can be difficult to control. To generate enhancement, the crystals are thousands of layers thick. As described herein, a means of generating 3-D confinement can be achieved using several layers of nanoparticles.

Figure 5:
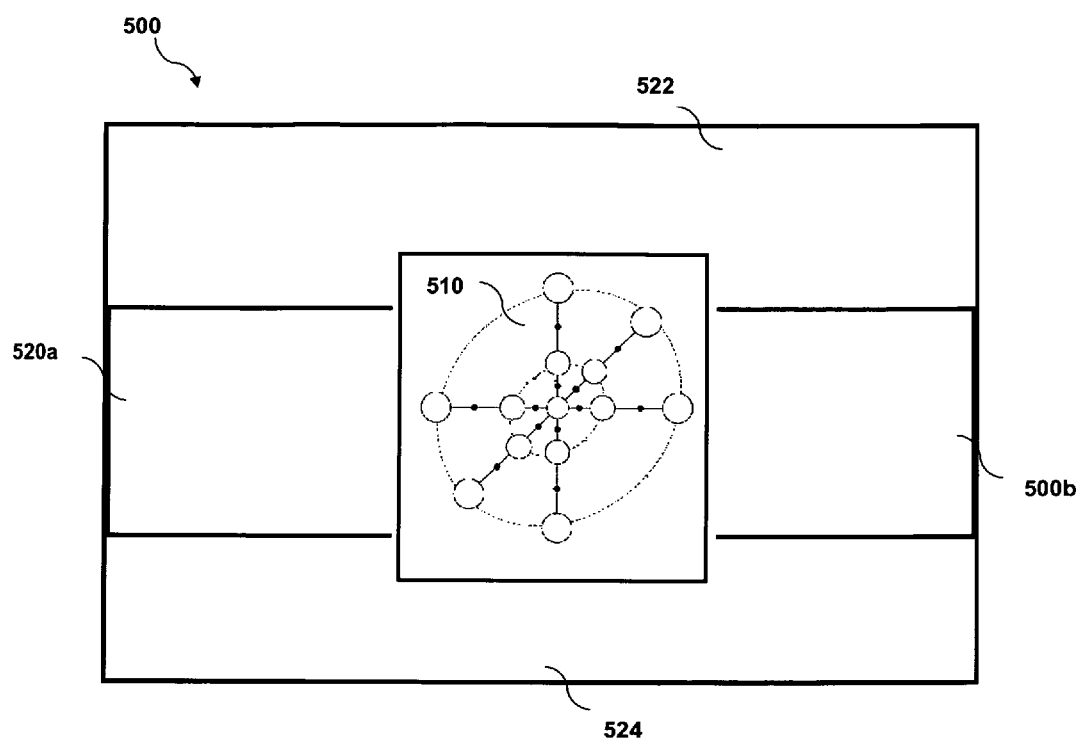
FIG. 5 are high level diagrams showing an exemplary embodiment of the injection structure.

FIG. 5 is an example of a preferred embodiment of the injection structure 500 where the structure could be made from polymer or semiconductor. In this embodiment, insulating layers 520a, 520b are on either side of the nanostructure 510. On opposing sides of the nanostructure are also a p-doped layer 522, and an n-doped layer 524. Current passes through the laser structure by tunneling. The resonator structure could be embedded in polymer or other materials to provide support in this embodiment as well.

Figure 6:
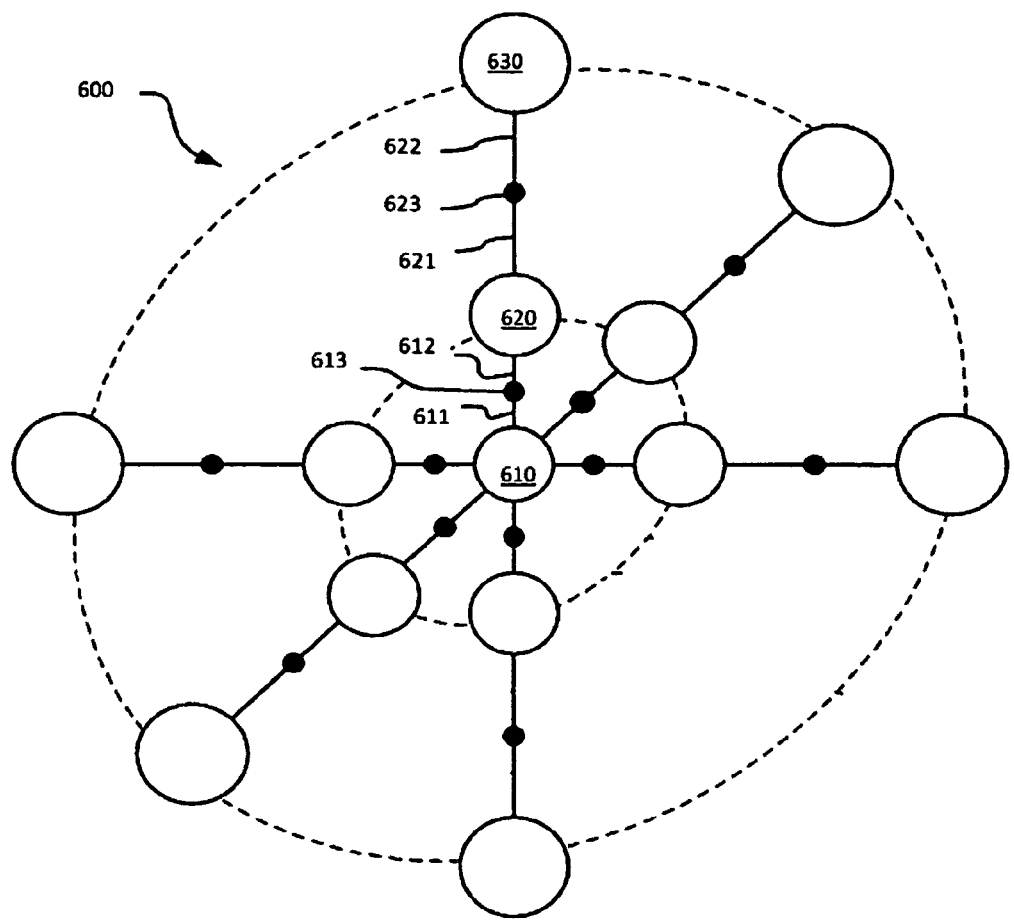
FIG. 6 is a diagram of a working example of the nanostructure having two tiers of metal nanoparticles.

Embodiments of the invention are illustrated further by the following working example, described with reference to FIG. 6:

EXAMPLE 1

An example nanostructure 600 could start with a photocatalytic nanoparticle 610 of Cadmium Selenide (CdSe). CdSe, as synthesized, has a bulk surface coating of trioctylphosphine oxide (TOPO). This can be removed and replaced with another ligand by a process of mass action. To a concentrated solution of CdSe, a 10× volume of pyridine may be added. This can then heated to 40 to 50° C. overnight to allow for ligand exchange, e.g. removal of the TOPO and replacement with pyridine. After 24 hours, the pyridine coated CdSe nanoparticles can be precipitated by the addition of methanol, and centrifuged at 2500 rpm for 20 minutes (until the supernate is colorless). The methanol can be decanted, at which point the required linker 611 can be added. For this example the linker 611 might be 4-aminothiophenol. This solution could then be heated at 40 to 50° C. overnight. After 24 hours octanol may be added to precipitate the CdSe nanoparticles coated with the linker 611, the flocculent solution is then centrifuged to pellet, the supernate decanted, and the isolated linker 611 coated CdSe resuspended in toluene. The photocatalytic nanoparticle 610 of CdSe is now completed and ready to be used for further assembly.

At this point, a second linker 612 can be attached to a first metal nanoparticle 620. In the present example, gold (Au) nanoparticles could be used as the first metal nanoparticle 620. Gold (Au) nanoparticles, as synthesized from a triphosphineogold oxonium salt [O(AuPPh3)3]BF4, have a bulk surface coating of hexadecylamine (HDA). This can be removed and replaced with another ligand by a process of mass action. To a concentrated solution of HDA coated gold nanoparticles, a 10× volume of pyridine may be added. This may then be heated to 40 to 50° C. overnight to allow for ligand exchange, e.g. removal of the HDA and replacement with pyridine. After 24 hours, the pyridine coated gold nanoparticles may be precipitated by the addition of methanol, and centrifuged at 2500 rpm for 20 minutes (until the supernate is colorless). The methanol may be decanted, and the required linker 612 added. For this example the linker 612 might be 4-mercaptobenzoic acid activated with dicyclohexylcarbodiimide (DCC). This solution could then be heated at 40 to 50° C. overnight. After 24 hours octanol can be added to precipitate the CdSe nanoparticles coated with linker 611, the flocculent solution may then be centrifuged to pellet, the supernate decanted, and the isolated linker 611 coated CdSe resuspended in toluene. The metal nanoparticle 620 of gold is now completed and ready to be used for further assembly. A third linker 621 can be attached to a first metal nanoparticle 620 in the same way as the second linker 612 is attached.

At this point, the gold metal nanoparticle 620 may be attached to the CdSe photocatalytic nanoparticle 610. To the solution of linker 611 coated CdSe nanoparticles 610, a solution of linker 612 coated gold nanoparticles 620 may be added drop wise in anhydrous toluene at a 1:6 molar ratio and heated to 40 to 50° C. for 36 hours. The exposed amine and activated carboxylic acid moieties from the respective attached CdSe and gold particle linkers 611, 612 may undergo a condensation reaction producing dicyclohexyl urea. Once the reaction time is complete, the coupled particle superstructure may be isolated and purified by precipitation from an 33/66% solution of ethanol/octanol and centrifuged to pellet. Once the supernate is decanted, the coupled particle superstructure can be resuspended in toluene and ready for use or further assembly.

At this point, a third linker 621 can be attached to the gold metal nanoparticle. As described above, gold (Au) nanoparticles 620, from [O(AuPPh3)3]BF4, have a bulk surface coating of hexadecylamine (HDA). This can be removed and replaced with another ligand, different from the activated carboxylic acid described above. Thus, to a concentrated solution of HDA coated gold nanoparticles 620, a 10× volume of pyridine may be added. This solution can then be heated to 40 to 50° C. overnight to allow for ligand exchange, e.g. removal of the HDA and replacement with pyridine. After 24 hours, the pyridine coated gold nanoparticles are precipitated by the addition of methanol, and centrifuged at 2500 rpm for 20 minutes (until the supernate is colorless). The methanol is decanted, and an amine linker 621 added. For this example the linker 621 might be 4-aminothiophenol. This solution could then be heated at 40 to 50° C. overnight. After 24 hours octanol may be added to precipitate the gold nanoparticles 610 coated with linker, the flocculent solution may then be centrifuged to pellet, the supernate decanted, and the isolated linker coated gold resuspended in toluene. The metal nanoparticle 620 is now completed and ready to be used for further assembly.

At this point, a fourth linker 622 may be attached to a second metal nanoparticle 630 and the third linker 621 and fourth linker 622 may be used to couple metal nanoparticle 620 to metal nanoparticle 630. To a solution of linker coupled particle superstructure, a solution of amine linker coated gold nanoparticles 610 may be added drop wise in anhydrous toluene at a 1:6 molar ratio and heated to 40 to 50° C. for 36 hours. The exposed activated carboxylic acid moieties remaining on the surface of the coupled particle superstructure may react with the amine functional group from the respective gold particle linkers and undergo a condensation reaction producing dicyclohexyl urea. Once the reaction time is complete, the coupled particle superstructure may be isolated and purified by precipitation from an 50/50% solution of ethanol/octanol and centrifuged to pellet. Once the supernate is decanted, the nanoparticle 600 is resuspended in toluene and ready for use.

In some embodiments of the above example, it may be desirable for like linkers to not attach to one another. Utilizing peptide bond chemistry, specific orientation, e.g. 'lock-n-key', to the nanoparticles can be attributed as the chemistry can only be amine to carboxylic acid coupled. Thus incorrect orientations such as CdSe to CdSe or gold to gold coupling might want to be avoided in creating the coupled particle superstructure as described above. In addition to the one way directional nature of the peptide bond, steric hindrance may also utilized to control spatial orientation. Since a nanoparticle and its surface ligands occupies volume, geometrically it is a spherical in shape. As the functional groups are only on the surface of this sphere (exposed ends of the linkers), and solid spheres interact tangential to a plane, two spheres can only interact at a single point. Molecularly, this limits the number of surface chemical groups that can react from between one to four depending on size of the two nanoparticles (curvature of the surface is respective to the radius). Thus only between 5 to 7 gold nanoparticles can fit around a single photocatalytic nanoparticle and make tangential contact (chemically couple). Due to the 'lock-n-key' nature of the peptide bond formation, coupling between the 6 to 8 metal nanoparticles in proximity once coupled to the photocatalytic particle will not occur. Finally, this superstructure may now present an exposed surface of DCC activated carboxylic acids for a further shell of metal nanoparticles functionalized with an amine terminated moiety to be added if required. Once again, because of 'lock-n-key' nature of the peptide coupling reaction and the tangential spatial spherical surface interaction, the current shell (n) being added can only do chemistry to the previous shell (n-1) and cannot add to an earlier shell (n-2).

The sulfur moiety chosen for attachment of the linkers to both exampled nanoparticles, CdSe and gold, is suitable chemistry to bind to other metal nanoparticles as well. These could include nanoparticles created from silver, aluminum, copper, titanium, or chromium.

Since the electronic or optical properties of the overall super molecular structure 'device' may require specific placement of the metal nanoparticle shells 620 relative to the photocatalytic nanoparticle center 610 and each respective shell, linker length may need to be changed between the shells. Since the total spacing between the shells is the molecular length of the coupled surface ligands, use of an additional ligand different from those utilized in the example above may be required. For example, a replacement ligand for the second gold nanoparticle shell with twice the radial spacing could be utilized from reduced 4'-amino-4-biphenylsulfonyl fluoride producing 4'-amino-4-biphenylthiol. Utilization of the 4-aminothiophenol, 4-mercaptobenzoic acid, 4-aminothiophenol system will provide a symmetric shell spacing $d1=d2$ while the 4-aminothiophenol, 4-mercaptobenzoic acid, 4'-amino-4-biphenylthiol provides for $d1<d2$ shell spacing. Other shell spacings can be generated from other oligomer type molecules with repeating units. A further example would be short chain polyethylene glycol derivatives.

One of the disadvantages of prior art nanotechnology inventions is the wide range of variability that can occur when using fewer particles in metal-semiconductor assemblies. Alexander O. Govorov,*,† Garnett W. Bryant,‡ Wei Zhang,† Timur Skeini,† Jaebeom Lee,§ Nicholas A. Kotov,§ Joseph M. Slocik,| and Rajesh R. Naik| Exciton-Plasmon Interaction and Hybrid Excitons in Semiconductor-Metal Nanoparticle Assemblies, 6 NANO Letters 984 (2006). According to Govorov et al., optical emissions of smaller metal-semiconductor assemblies are modified strongly by interparticle coulomb interaction. Id. Govorov et al., goes on to describe that the interaction between individual nanoparticles is revealed as an enhancement or suppression of emission. Id. Enhanced emission comes from electric field amplified by the plasmon resonance, whereas emission suppression is a result of energy transfer from semiconductor to metal nanoparticles. Id. The emission intensity and energy transfer rate depend strongly on the geometrical parameters of the superstructure and the physical and material properties of the nanoparticles. In particular, the emission enhancement effect appears for nanoparticles with relatively small quantum yield, and silver nanoparticles have stronger enhancement compared to gold ones. Id.

One of the general aspects of this embodiment of the invention is that it avoids the uncertainty and variability that concerned Govorov et al., through two factors (1) containment of the field and (2) decreasing the flexibility of the linker systems. The first factor, containment of the field, literally refers to the containment properties that the numerous particles 620 provide simply by surrounding the inner particle 610. As discussed in reference to FIGS. 3, 4a, and 4b, the wavelength graphs show that the more particles, the narrower the enhanced emission window. By using conjugated aromatics, this embodiment of the present invention is stiff and resistant to bending. Therefore it is more dimensionally stable, less prone to temperature variations, and thus, reduces homogeneous broadening which was troublesome in the prior art.

It will be apparent to those skilled in the art that various changes and modifications can be made in the method and system for accumulating and presenting device capability information of the present invention without departing from the spirit and scope thereof. Thus, it is intended that the invention cover the modifications of this invention provided they come within the scope of the appended claims and their equivalents.

What is claimed is:

1. A nanostructure comprising:
   a photocatalytic nanoparticle comprised of a semiconductor material;
   a first tier of metal nanoparticles said metal selected from the group consisting of gold, silver, and copper, each metal nanoparticle of the first tier being linked about the photocatalytic nanoparticle; and
   a second tier of metal nanoparticles said metal selected from the group consisting of gold, silver, and copper, each metal nanoparticle of the second tier being linked to one of the metal nanoparticles of the first tier and located a distance from the photocatalytic nanoparticle greater than a distance between a metal nanoparticle of the first tier and the photocatalytic nanoparticle, wherein
   at least one first linker comprising a condensation product of a linker having an amine fuctional group and a linker having a carboxylic acid functional group is attached to the photocatalytic nanoparticle;
   a second linker comprising a condensation product of a linker having an amine functional group and a linker having a carboxylic acid functional group is attched to each metal nanoparticle of the first tier;
   a third linker comprising a condensation product of a linker having an amine functional group and a linker having a carboxylic acid functional group is attached to each metal nanoparticle of the first tier; and
   a fourth linker comprising a condensation product of a linker having an amine functional group and a linker having a carboxylic acid functional group is attached to second metal nanoparticles of the second tier, wherein like ones of the first through fourth linkers do not attach to one another.

2. The nanostructure according to claim 1, wherein the photocatalytic nanoparticle is a quantum dot.

3. The nanostructure according to claim 1, wherein the semiconductor material comprises a heterojuntion.

4. The nanostructure according to claim 1, wherein the metal nanoparticles are comprised of gold.

5. The nanostructure according to claim 1, wherein the nanostructure is located in a dielectric medium.

6. The nanostructure according claim 5, wherein the medium shifts the resonant wavelength of the nanostructure.

7. The nanostructure according to claim 5, wherein dielectric constant of the dielectric medium is adjustable.

8. The nanostructure according to claim 1, wherein metal nanoparticles of the first and second tiers are coated with a material having a dielectric constant different from a dielectric constant of the metal nanoparticles.

9. The nanostructure according to claim 1 where the first through fourth linkers are polyethylene glycol (PEG) linkers.

10. The nanostracture according to claim 1, wherein the size of metal nanoparticles of the first group is different from the size of the metal nanoparticles of the second tier.

11. The nanostructure according to claim 10, wherein metal nanoparticles of the second tier are larger than metal nanoparticles of the first tier.

12. A method for assembling a nanostructure, comprising:
attaching a first linker comprising a condensation product of a linker having an amine functional group and a linker having a carboxylic acid functional group is to a photocatalytic nanoparticle, wherein said photocatalytic nanoparticle is comprised of a semiconductor material;
attaching a second linker comprising a condensation product of a linker having an amine functional group and a linker having a carboxylic acid functional group is about a first metal nanoparticle, said metal of said first metal nanoparticle being selected from the group consisting of gold, silver, and copper;
attaching the first metal nanoparticle about the photocatalytic nanoparticle by connecting the first linker and the second linker;
attaching a third linker comprising a condensation product of a linker having an amine functional group and linker having a carboxylic acid functional group is to a first metal nanoparticle;
attaching a fourth linker comprising a condensation product of a linker having an amine functional group and a linker having a carboxylic acid functional group is to a second metal nanoparticle said metal of said second metal nanoparticle being selected from the group consisting of gold, silver, and copper; and
attaching the second metal nanoparticle to the first metal nanoparticle by connecting the third linker and the fourth linker.

13. The method according to claim 12, wherein like ones of the first through fourth linkers do not attach to one another.

14. The method according to claim 12, wherein the metal nanoparticles are comprised of gold.

15. The method according to claim 12, wherein the first, second, third, and fourth linkers are each of a same length.

16. The method according to claim 12, wherein the first and third linkers have one end terminating in a carboxylic acid group.

17. The method according to claim 12, wherein the second and fourth linkers have one end terminating in an amine group.

18. The nanostructure according to claim 1, wherein the metal nanoparticles are comprised of silver.

19. The nanostructure according to claim 1, wherein the metal nanoparticles are comprised of copper.

20. The method according to claim 12, wherein the metal nanoparticles are comprised of silver.

21. The method according to claim 12, wherein the metal nanoparticles are comprised of copper.

* * * * *